United States Patent [19]

Sota

[11] Patent Number: 5,546,182

[45] Date of Patent: Aug. 13, 1996

[54] METHOD FOR DETERMINATION OF TRACE METAL IMPURITY IN FLUORINE-CONTAINING POLYMER AND PROCESS FOR PRODUCTION OF FLUORINE-CONTAINING POLYMER USING THE METHOD

[75] Inventor: Tomizo Sota, Osaka, Japan

[73] Assignee: Daikin Industries Ltd., Osaka, Japan

[21] Appl. No.: 374,634

[22] PCT Filed: May 20, 1994

[86] PCT No.: PCT/JP94/00809

§ 371 Date: Mar. 9, 1995

§ 102(e) Date: Mar. 9, 1995

[87] PCT Pub. No.: WO94/28394

PCT Pub. Date: Dec. 8, 1994

[30] Foreign Application Priority Data

May 21, 1993 [JP] Japan .................. 5-119456

[51] Int. Cl.⁶ .......................... G01N 21/31; G01N 21/74
[52] U.S. Cl. ............................... 356/312; 356/36
[58] Field of Search ..................... 356/36, 311, 312

[56] References Cited

U.S. PATENT DOCUMENTS 4,912,528  3/1990  Hwang et al. .................. 356/312

FOREIGN PATENT DOCUMENTS 60-230041  11/1985  Japan .
62-233742  10/1987  Japan .
2-091570   3/1990   Japan .

OTHER PUBLICATIONS

Pre-print of 33rd Annual Meeting of Japanese Analytical Chemistry Association, 1 A 11, p. 409 (1984).

*Primary Examiner*—F. L. Evans
*Attorney, Agent, or Firm*—Birch, Stewart, Kolasch & Birch, LLP

[57] ABSTRACT

In order to quantitatively determine a metal impurity contained in a fluorine-containing polymer directly, and also to improve a detection limit of the metal quantitative determination, there is provided a method for the quantitative determination of a trace amount of a metal impurity contained in a fluorine-containing polymer using a flameless atomic absorption spectrophotometer wherein a predetermined amount of a sample of the polymer containing the metal to be quantitatively determined is incinerated under incineration conditions including an incineration temperature in the range of about 400° to 1200° C. and an incineration period of at least about 100 seconds, and then an absorbance of the incinerated sample as such is measured using the flameless atomic absorption spectrophotometer. In addition, there are provided a process for the production of the fluorine-containing polymer characterized in that the trace amount of the metal impurity contained in the fluorine-containing polymer is quantitatively monitored by means of the method, and a process for the production of the fluorine-containing polymer characterized in that the trace amount of the metal impurity contained in the fluorine-containing polymer is quantitatively determined by means of the method according to the method.

5 Claims, No Drawings

METHOD FOR DETERMINATION OF TRACE METAL IMPURITY IN FLUORINE-CONTAINING POLYMER AND PROCESS FOR PRODUCTION OF FLUORINE-CONTAINING POLYMER USING THE METHOD

TECHNICAL FIELD

The present invention relates to a method for the determination of a trace amount of a metal impurity contained in a fluorine-containing polymer (fluoropolymer), especially the quantitative determination of a metal impurity contained in a trace amount in a fluorine-containing polymer by using a so-called flameless atomic absorption spectrophotometer, and a process for the production of a fluorine-containing polymer with using said method.

DISCLOSURE OF THE INVENTION

Fluorine-containing polymers are used in various industrial fields, and it is very often that trace amounts of metals contained in the polymers as impurities such as iron, copper, nickel, sodium, potassium and so on cause problems. For example, in a semiconductor relating field, a fluorine-containing polymer such as a tetrafluoroethylene/perfluoro-(alkyl vinyl ether) copolymer (which is, hereinafter, referred to as "PFA") is used for a basket wherein a leak error may be caused in a P-N bonding when the trace amounts of the metals such as iron, copper, nickel and so on are dissolved out and they are present in a semiconductor device.

In addition, since an alkaline metal such as sodium, potassium and so on is likely to cause insufficient withstand voltage of an oxide film, it is important to know the amounts of the metals contained in the fluorine-containing polymer. Further, also during production of the fluorine-containing polymer, it is sometimes necessary to determine the trace amounts of the metals contained in the fluorine-containing polymer so as to ensure operation controls.

A method which has been hitherto used so as to quantitatively determine trace amounts of metals contained in a fluoroplastic comprises charging the fluoroplastic to be determined into a platinum made evaporating dish (of which platinum purity is usually 99.9%), incinerating the fluoroplastic with a burner or in an electrical furnace, and then dissolving a residue of the trace metals into a solution, which is subjected to the atomic absorption spectrophotometry so as to quantitatively determine the amount of the metals.

However, the above method has problems that it requires to use a large amount of the fluoroplastic and that its recoveries of metal elements are not so high. In addition, the platinum made evaporating dish is eroded by decomposition gases which are produced, when the incineration is carried out, which erosion causes a contamination problem by impurities contained in the evaporating dish. Alternatively, even though the evaporating dish is completely cleaned, there may occur a phenomenon that metals of the previous determination still remain on the dish (which is so-called "memory effect"). Therefore, these problems make it impossible to quantitatively and precisely determine the trace metals contained in the fluoroplastic.

On the basis of the above prior arts, trials have been carried out so as to make it possible to directly carry out quantitative determination of a trace amount of a transition metal contained in a fluoroplastic (see Pre-print of 33 rd Annual Meeting of Japanese Analytical Chemistry Association, 1 A 11, page 409 (1984)). This reference describes as follows: Even though direct quantitative determination of the trace amount of the metal contained in the fluoroplastic is carried out using a Zeeman graphite furnace atomic absorption spectrophotometer, detection of the metal is impossible since the metal contained in the polymer is volatilized out as a fluoride. However, such a trace metal can be stably detected when a metal sulfate thereof is produced under the coexistence of an inorganic additive such as $KHSO_4$ during dry incineration.

In such a method, a temperature of about 1000° C. is employed as a dry incineration temperature, and a detection limit of the metal is said to be about 20 ppb in the case of a sample amount of 10 mg. However, in this method, the addition of $KHSO_4$ as an additional step is required, which provides another possibility of contamination, and further the detection limit of the metals is so relatively high as 20 ppb.

It is, therefore, desirable to provide a quantitative determination method of the trace amount of the metal impurities contained in the fluorine-containing polymer which method can be carried out truly directly. In addition, it is desirable that such a quantitative determination method has a further improved metal detection limit.

DISCLOSURE OF THE INVENTION

Thus, the present inventor has made intensive studies on an analytical method for the trace amounts of the metals contained in the fluorine-containing polymers, and found that, in a method for the quantitative determination of metal impurities contained in the .fluorine-containing polymers using a flameless atomic absorption spectrophotometer, the quantitative determination of the trace amounts of the-metal impurities contained in the fluorine-containing polymers is directly achieved with a lower detection limit such as 1 ppb or less when specified incineration conditions are employed.

That is, the present invention provides a method for the quantitative determination of a trace amount of a metal impurity contained in a fluorine-containing polymer (fluoropolymer) using a flameless atomic absorption spectrophotometer wherein, depending on a kind of a metal to be quantitatively determined, a predetermined amount of a sample of the polymer is incinerated under incineration conditions including an incineration temperature in the range of about 400° to 1200° C. and an incineration period of at least about 100 seconds, preferably in the range of about 100 to 1200 seconds, and then an absorbance of the incinerated sample is measured using the flameless atomic absorption spectrophotometer.

Further, the present invention provides a process for the production of a fluorine-containing polymer wherein an amount of a metal impurity contained in the fluorine-containing polymer is quantitatively monitored by means of the method as just described above, and also a process for the production of a fluorine-containing polymer wherein an amount of a metal impurity contained in the fluorine-containing polymer is quantitatively determined by means of the method as just described above.

DETAILED DESCRIPTION OF THE INVENTION

In the present invention, the term "direct(ly)" is intended to mean that, during the determination procedure, a sample to be determined is subjected to no specific chemical treatment except the incineration treatment prior to the measurement using the atomic absorption spectrophotometry. Thus, the term is not intended to exclude, for example, a drying step of a sample of the fluorine-containing polymer to be determined prior to the incineration.

In the present invention, the flameless atomic absorption spectrophotometer means a spectrophotometer, in which a sample is electrically heated so as to atomize metals contained therein (for example, an electrical current is passed through a graphite made cuvette so that the sample is heated so as to atomize the metals), and amounts of metals are quantitatively measured based on absorbances of the atomized metals. Usually, the determination is carried out in such a manner that a drying step is carried out as a pre-treatment so as to remove moisture and volatile solvents; then an incineration step is carried out so as to decompose and remove organic compounds; and then an atomizing step is carried out followed by the absorption measurement. When the pre-treatment is insufficient, elements to be determined are volatilized explosively during the atomizing step, so that the measurement may be impossible. Concretely, the determination may be carried out by means of, for example, a so-called Zeeman graphite furnace atomic absorption spectrophotometer.

In the present invention, the fluorine-containing polymer is intended to mean a polymer of which molecular weight is in the range of about 1000 to 9000000 (nine million), and of which side chain is a perfluoro group or includes a fluorine atom and a hydrogen atom. Such a polymer includes a polymer material which contains fluorine such as a plastic material, a rubber material or an oil material and so on. Concrete examples of the fluorine-containing polymer include a polytetrafluoroethylene, a tetrafluoroethylene/perfluoro(alkyl (for example, propyl and so on) vinyl ether) copolymer, a tetrafluoroethylene/hexafluoropropylene copolymer, a tetrafluoroethylene/ethylene copolymer, a polyvinylidene fluoride, a polyvinyl fluoride, a vinylidene fluoride/tetrafluoroethylene/hexafluoropropylene copolymer, a vinylidene fluoride/hexafluoropropylene copolymer, a tetrafluoroethylene/perfluoro(alkyl (for example, methyl, propoxyl and so on) vinyl ether) copolymer or a perfluoropolyether and so on.

The metal of a trace amount contained in the fluorine-containing polymer which can be quantitatively determined by the method according to the present invention is not specifically limited, and it includes any metal which is generally quantitatively determined by means of the flameless atomic absorption spectrophotometer. Concretely, the metals such as Fe, Cr, Ni, Cu, Na, K, Mg, Ca, Co, Zn, Mn and Al are quantitatively determined.

In the present invention, the term "trace (amount)" is used to mean that a concentration of the order of "ppm" or less, for example, a concentration of the order of a "ppb" is determined, but it does not mean that a metal concentration which is higher than such a low concentration cannot be determined. Thus, in the present invention, the term "trace (amount)" generally and merely means that the present invention is useful for the quantitative metal determination in the order of the "ppm" or "ppb" concentration.

In the present invention, the term "incineration (ashing)" means that an organic material such as the fluorine-containing polymer thermally decomposed and volatilized so that an inorganic material(s) is left.

An amount of the sample of the-fluorine-containing polymer to be determined depends on the "incineration conditions", and it is properly selected on the basis of the incineration conditions. Considering the use of a commercially available flameless atomic absorption spectrophotometer and the advantage of a small amount of the sample to be used in the flameless atomic absorption spectrophotometer, the amount of the sample to be used for the determination is generally in the range of 0.1 to 20 mg, preferably in the range of 0.5 to 10 mg, and more preferably in the range of 1 to 5 mg.

In addition, a kind of the fluorine-containing polymer to be determined also depends on the "incineration conditions". Generally, the fluorine-containing polymer consisting essentially of fluorine and carbon requires severer incineration conditions (relatively longer period and/or higher temperature). To the contrary, more moderate conditions (relatively shorter period and/or lower temperature) are sufficient for the polymer containing much hydrogen (H) and oxygen (O).

In the present invention, the "incineration condition(s)" includes any condition which is required to incinerate the fluorine-containing polymer, and conditions (for example, a temperature increasing rate, the presence or absence of $O_2$ in an incineration atmosphere, a flow rate setting of a carrier gas) employed in the conventional atomic absorption spectrophotometry are applied with exceptions of the incineration temperature and the incineration period.

In the present invention, the term "incineration period" means a period during which the fluorine-containing polymer sample to be determined is heated so as to substantially decompose and remove materials except metals contained in the polymer. When the sample contains moisture, the sample should be dried so as to remove the moisture. A period required for such drying is not included in the incineration period. The term "substantially" herein means "in such an extent that an accuracy and a detection limit of the intended quantitative determination are not affected". Such an "incineration period" is selected depending on a kind and the amount of the fluorine-containing polymer to be determined. In the present invention, the "incineration period" is at least about 100 seconds and for example, it may be not less than 640 seconds. Generally, an upper limit of the "incineration period" is about 1200 seconds. Such an "incineration period" of the present invention is a considerably long period which cannot be expected at all when it is considered that an incineration period in the range of about 30 to 60 seconds has been employed in the conventional determination using the flameless atomic absorption spectrophotometer.

From a view point that the metals contained in the fluorine-containing polymer cannot be detected since they are volatilized as the fluorides during the incineration treatment as described in the above, it could be expected that carrying out the incineration treatment for an extended period itself would make the detection limit of the metals worse and worse. However, contrary to such an expectation, the present invention has surprisingly improved the detection limit of the metals contained in the fluorine-containing polymer by means of the long period of the incineration treatment.

In the present invention, the term "incineration temperature" means a temperature to which the fluorine-containing sample to be determined is heated so as to remove materials except the metals contained therein, for example so as to decompose them substantially as they are or to decompose them with combustion. Such an "incineration temperature" may be properly selected depending on the kind and the amount of the fluorine-containing polymer to be determined.

As described in the above, the incineration conditions depend on the kind and the amount of the fluorine-containing polymer to be determined. The incineration period is generally at least about 100 seconds, preferably in the range of about 100 to 1200 seconds, more preferably in the range of about 100 to 640 seconds and most preferably in the range of about 120 to 300 seconds, and the incineration temperature is generally in the range of about 400° to 1200° C. and preferably in the range of about 800° to 1200° C.

These "incineration temperature" and "incineration period" can be selected on the basis of the following.

Generally, when the incineration temperature is lower or the incineration period is shorter, the incineration is likely to be insufficient so that the polymer remains and thus there comes to no condition in which the materials except the metals are substantially decomposed and removed. In such a condition, the materials in addition to the metals still remain up to the atomizing step of the atomic absorption spectrophotometry and such materials are decomposed at once during the atomizing step so that a phenomenon is observed on the spectrophotometry measurement as if a large amount of metals were present.

To the contrary, when the incineration temperature is higher, the decomposition proceeds at once during the incineration step so that the impurity metals are also removed with being entrained out by produced decomposition gases, which causes a behavior on the spectrophotometry measurement as if the metal impurities were not present.

Thus, a standard sample of which metal concentration has been already known is prepared beforehand, and various incineration conditions except extreme conditions as described above are applied to such a sample so that the incineration conditions including the sample amount, the incineration temperature, the incineration period and so on are selected depending on the kind of the fluorine-containing polymer which conditions achieve a predetermined recovery (a ratio of an actually determined concentration by the atomic absorption spectrophotometer to the known concentration, for example at least 70%). However, it is especially preferable in the present invention that the incineration temperature and the incineration period are in the specified range as described in the above.

A form of the sample for the determination is not specifically limited in the present method. For example, even when the sample is in the form of a block-like such as a pellet or a powder form, the determination is possible. It should be noted that the incineration conditions may have to be changed depending on the sample form. Generally, when the sample is in the form of the powder, uniform heating is possible and each particle of the sample is likely to contact with oxygen, which leads to relatively moderate incineration conditions.

The present method uses a cuvette (cell) into which the sample for the determination is to be charged in the incineration step and in the atomic absorption spectrophotometry analysis step thereafter. Any type of the cuvette may be used, and for example, a cup type or a tube type cuvette may be used. A material of which the cuvette is made is preferably graphite. In addition, a particularly preferred cuvette is one which has been subjected to a pyro-treatment. The term "pyro-treatment" means a treatment in which a surface of the graphite cuvette is coated with an ultra-dense graphite.

Generally, a carrier gas is used on the incineration and the atomic absorption spectrophotometry analysis. Also in the method of the present invention, the carrier gas which is conventionally used such as argon and argon $+O_2$ is used. Since a flow rate of the carrier gas may affect the analysis accuracy, a proper carrier gas flow rate may be selected under consideration of recovery (recovery ratio) changes with varying the carrier gas flow rate. Generally, the gas is supplied at a flow rate in the range of about 10 to 200 ml/min. and preferably about 50 to 200 ml/min. during the incineration step. The gas is preferably supplied at a flow rate in the range of about 10 to 30 ml/min. during the atomizing step.

According to the method of the present invention, it is possible that the metal content in the trace amount is determined with a further smaller detection limit than that of the prior art. Concretely, in the case where the amount of the sample is in the range of 1 to 5 mg, the detection limit for Fe is about 1 ppb as shown in Example 12, and similarly about 1 ppb for Cr, about 1 ppb for Ni, about 1 ppb for Cu, about 1 ppb for Na, about 1 ppb for K and about 1 ppb for Mg, which are all much improved compared with the prior art detection limit of about 20 ppb. In addition, the larger the amount of the used sample is, the lower the detection limit becomes. For example, when the amount of the sample is approximately doubled, the detection limit is roughly halved.

Next, particularly preferred incineration conditions will be exemplified for the quantitative determination of the trace metals contained in the fluorine-containing polymer using the method according to the present invention. Though the preferred conditions depend on the amount of the sample, the following examples are for the case in which the amount of the sample is in the range of about 1 to 5 mg.

For a polytetrafluoroethylene (PTFE), a sufficient long incineration period at a relatively elevated temperature is required after the drying step of the sample. The incineration operation may be carried out by heating the sample under the preferred incineration conditions of the incineration temperature in the range of 800° to 1200° C. over the incineration period not shorter than 100 seconds. This period may be extended up to 1200 seconds, which causes no problem against the metal quantitative determination. However, a period shorter than 100 seconds, for example 60 seconds leads to insufficient incineration, which makes the quantitative determination of the metals impossible.

For a tetrafluoroethylene/perfluoro(alkyl vinyl ether) copolymer (PFA), preferred incineration step conditions are substantially the same as those for PTFE.

For an ethylene/tetrafluoroethylene copolymer (ETFE), it is required that the incineration starts at a relatively low temperature after drying the sample, and then the temperature is gradually increased. As preferred incineration conditions, the following example may be used: starting to heat the sample at 400° C., heating to a temperature in the range between 400° C. and 600° C. for 60 seconds, and then heating to a temperature in the range between 800° C. and 1200° C. for 300 seconds.

Industrial Applicability

According to the method of the present invention, the quantitative determination for the metal impurities contained in the fluorine-containing polymer is carried out precisely, and also the detection limit of the method is improved compared with the prior art method. In addition, when the method of the present invention is applied to the production process for the fluorine-containing polymer, it is possible to quantitatively determine and monitor the trace amounts of the metal impurities contained in the produced fluorine-containing polymer, and also, for example, to judge a polymer quality with respect to the impurities contained in the polymer (for example, whether it is to be accepted or to be rejected) by means of the impurity contents, so that the method of the present invention is very effective-for the production of the polymer.

EXAMPLES

The present invention will be, hereinafter, explained more concretely with reference to Examples.

Example 1

Quantitative measurement of trace iron contained in a fluorine-containing polymer was carried out according to the method of the present invention with using a Zeeman graphite furnace atomic absorption spectrophotometer (Z-8100, commercially manufactured by HITACHI, Ltd.) as the atomic absorption spectrophotometer.

The fluorine-containing polymer used in this example was polytetrafluoroethylene (PTFE, molecular weight: about eight million).

Incineration conditions and atomizing conditions of this examples are shown in Table 1 below:

[TABLE 1]

| Treatment Step | Initial Heating Temperature | Final Heating Temperature | Heating Period | Carrier Gas Amount |
| --- | --- | --- | --- | --- |
| drying | 80° C. | 120° C. | 30 seconds | 200 ml/min. |
| incineration | 800° C. | 1000° C. | 60 seconds | 50 ml/min. |
| incineration | 1000° C. | 1100° C. | 60 seconds | 50 ml/min. |
| incineration | 1100° C. | 1100° C. | 60 seconds | 50 ml/min. |
| incineration | 1100° C. | 1100° C. | 60 seconds | 50 ml/min. |
| atomizing | 2700° C. | 2700° C. | 10 seconds | 30 ml/min. |
| cleaning | 2800° C. | 2800° C. | 4 seconds | 200 ml/min. |

In above Table 1, "cleaning" means a treatment in which remaining elements are completely volatilized at a temperature which is higher by 100° to 200° C. than the atomizing temperature.

In this example, a predetermined amount (10 μl) of an aqueous solution containing iron at a predetermined concentration (Fe concentration: 20 ppb) was added in a sample of an amount shown in Table 2 below with a micro-syringe so that an iron-containing resin was prepared, and its iron concentration was measured. A cuvette used here was a tube type one which had been subjected to a pyro-treatment. Ar was used as a carrier gas. The results are shown in Table 2 below:

[TABLE 2]

| Sample | Added Fe | Detected Fe | Recovered Fe | Recovery |
| --- | --- | --- | --- | --- |
| 2.54 mg | — | 14 pg | — | — |
| 3.11 mg | 200 pg | 179 pg | 162 pg | 81% |
| 3.35 mg | 200 pg | 180 pg | 162 pg | 81% |
| 4.12 mg | 200 pg | 190 pg | 168 pg | 84% |

"Added Fe" means an amount of Fe contained in the added aqueous solution.

"Detected Fe" means a detected amount of Fe converted from an iron concentration measurement practically obtained by the method according to the present invention.

"Recovered Fe" means a difference amount of the Detected Fe amount minus an amount of Fe of the resin without the addition of Fe (namely, the Detected Fe amount minus an amount of Fe originally contained in the resin).

Recovery=(Recovered Fe / Added Fe)×100

Example 2

Using the same apparatus as in Example 1, quantitative measurement of trace chromium contained in a fluorine-containing polymer was carried out according to the method of the present invention.

The fluorine-containing polymer used in this example was a PTFE (molecular weight: about eight million).

Incineration conditions and atomizing conditions of this examples are shown in Table 3 below:

[TABLE 3]

| Treatment Step | Initial Heating Temperature | Final Heating Temperature | Heating Period | Carrier Gas Amount |
| --- | --- | --- | --- | --- |
| drying | 50° C. | 100° C. | 60 seconds | 200 ml/min. |
| drying | 100° C. | 120° C. | 60 seconds | 200 ml/min. |
| incineration | 1000° C. | 1100° C. | 60 seconds | 200 ml/min. |
| incineration | 1100° C. | 1200° C. | 60 seconds | 200 ml/min. |
| incineration | 1200° C. | 1200° C. | 60 seconds | 200 ml/min. |
| incineration | 1200° C. | 1200° C. | 60 seconds | 200 ml/min. |
| atomizing | 2900° C. | 2900° C. | 10 seconds | 30 ml/min. |
| cleaning | 3000° C. | 3000° C. | 4 seconds | 200 ml/min. |

In this example, a predetermined amount (10 μl)of an aqueous solution containing chromium at a predetermined concentration (Ce concentration: 10 ppb) was added in a sample of an amount shown in Table 4 below with a micro-syringe so that a chromium-containing resin was prepared, and its chromium concentration was measured. A cuvette used here was a tube type one which had been subjected to a pyro-treatment. Ar was used as a carrier gas. The results are shown in Table 4 below:

[TABLE 4]

| Sample | Added Cr | Detected Cr | Recovered Cr | Recovery |
| --- | --- | --- | --- | --- |
| 3.35 mg | — | <1 pg | — | — |
| 2.63 mg | 100 pg | 97 pg | 97 pg | 97% |
| 3.06 mg | 100 pg | 80 pg | 80 pg | 80% |
| 3.63 mg | 100 pg | 71 pg | 71 pg | 71% |

"Added Cr" means an amount of Cr contained in the added aqueous solution.

"Detected Cr" means a detected amount of Cr converted from a Cr concentration measurement practically obtained by the method according to the present invention.

"Recovered Cr" means a difference amount of the Detected Cr amount minus an amount of Cr of the resin without the addition of Cr (namely, the Detected Cr amount minds an amount of Cr originally contained in the resin).

Recovery=(Recovered Cr / Added Cr)×100

Example 3

Using the same apparatus as in Example 1, quantitative measurement of trace nickel contained in a fluorine-containing polymer was carried out according to the method of the present invention.

The fluorine-containing polymer used in this example was a PTFE (molecular weight: about eight million).

Incineration conditions and atomizing conditions of this examples are shown in Table 5 below:

[TABLE 5]

| Treatment Step | Initial Heating Temperature | Final Heating Temperature | Heating Period | Carrier Gas Amount |
|---|---|---|---|---|
| drying | 50° C. | 130° C. | 60 seconds | 200 ml/min. |
| incineration | 800° C. | 1000° C. | 60 seconds | 50 ml/min. |
| incineration | 1000° C. | 1100° C. | 60 seconds | 50 ml/min. |
| incineration | 1100° C. | 1100° C. | 60 seconds | 50 ml/min. |
| incineration | 1100° C. | 1100° C. | 60 seconds | 50 ml/min. |
| atomizing | 2700° C. | 2700° C. | 10 seconds | 30 ml/min. |
| cleaning | 2800° C. | 2800° C. | 4 seconds | 200 ml/min. |

In this example, a predetermined amount (10 μl) of an aqueous solution containing nickel at a predetermined concentration (Ni concentration: 10 ppb) was added in a sample of an amount shown in Table 6 below with a micro-syringe so that a chromium-containing resin was prepared, and its nickel concentration was measured. A cuvette used here was a tube type one which had been subjected to a pyro-treatment. Ar was used as a carrier gas. The results are shown in Table 6 below:

[TABLE 6]

| Sample | Added Ni | Detected Ni | Recovered Ni | Recovery |
|---|---|---|---|---|
| 2.50 mg | — | <2 pg | — | — |
| 3.05 mg | 200 pg | 187 pg | 187 pg | 94% |
| 2.70 mg | 200 pg | 177 pg | 177 pg | 89% |
| 2.12 mg | 200 pg | 191 pg | 191 pg | 95% |

"Added Ni" means an amount of Ni contained in the added aqueous solution.

"Detected Ni" means a detected amount of Ni converted from an Ni concentration measurement practically obtained by the method according to the present invention.

"Recovered Ni" means a difference amount of the Detected Ni amount minus an amount of Ni of the resin without the addition of Ni (namely, the Detected Ni amount minus an amount of Ni originally contained in the resin).

Recovery=(Recovered Ni/Added Ni)×100

Example 4

Using the same apparatus as in Example 1, quantitative measurement of trace copper contained in a fluorine-containing polymer was carried out according to the method of the present invention.

The fluorine-containing polymer used in this example was a PTFE (molecular weight: about eight million).

Incineration conditions and atomizing conditions of this examples are shown in Table 7 below:

[TABLE 7]

| Treatment Step | Initial Heating Temperature | Final Heating Temperature | Heating Period | Carrier Gas Amount |
|---|---|---|---|---|
| drying | 50° C. | 130° C. | 60 seconds | 200 ml/min. |
| incineration | 800° C. | 1000° C. | 60 seconds | 50 ml/min. |
| incineration | 1000° C. | 1100° C. | 60 seconds | 50 ml/min. |
| incineration | 1100° C. | 1100° C. | 60 seconds | 50 ml/min. |

[TABLE 7]-continued

| Treatment Step | Initial Heating Temperature | Final Heating Temperature | Heating Period | Carrier Gas Amount |
|---|---|---|---|---|
| incineration | 1100° C. | 1100° C. | 60 seconds | 50 ml/min. |
| atomizing | 2700° C. | 2700° C. | 10 seconds | 30 ml/min. |
| cleaning | 2800° C. | 2800° C. | 4 seconds | 200 ml/min. |

In this example, a predetermined amount (10 μl) of an aqueous solution containing nickel at a predetermined concentration (Cu concentration: 10 ppb) was added in a sample of an amount shown in Table 8 below with a micro-syringe so that a nickel-containing resin was prepared, and its copper concentration was measured. A cuvette used here was a tube type one which had been subjected to a pyro-treatment. Ar was used as a carrier gas. The results are shown in Table 8 below:

[TABLE 8]

| Sample | Added Cu | Detected Cu | Recovered Cu | Recovery |
|---|---|---|---|---|
| 3.65 mg | — | <3 pg | — | — |
| 3.91 mg | 100 pg | 85 pg | 85 pg | 85% |
| 1.65 mg | 100 pg | 89 pg | 89 pg | 89% |
| 2.08 mg | 100 pg | 102 pg | 102 pg | 102% |

"Added Cu" means an amount of Cu contained in the added aqueous solution.

"Detected Cu" means a detected amount of Cu converted from a Cu concentration measurement practically obtained by the method according to the present invention.

"Recovered Cu" means a difference amount of the Detected Ni amount minus an amount of Cu of the resin without the addition of Cu (namely, the Detected Cu amount minus an amount of Cu originally contained in the resin).

Recovery=(Recovered Cu / Added Cu)×100

Example 5

Using the same apparatus as in Example 1, quantitative measurement of trace sodium contained in a fluorine-containing polymer was, carried out according to the method of the present invention.

The fluorine-containing polymer used in this example was a PTFE (molecular weight: about eight million).

Incineration conditions and atomizing conditions of this examples are shown in Table 9 below:

[TABLE 9]

| Treatment Step | Initial Heating Temperature | Final Heating Temperature | Heating Period | Carrier Gas Amount |
|---|---|---|---|---|
| drying | 80° C. | 150° C. | 50 seconds | 200 ml/min. |
| incineration | 800° C. | 1000° C. | 60 seconds | 50 ml/min. |
| incineration | 1000° C. | 1100° C. | 60 seconds | 50 ml/min. |
| incineration | 1100° C. | 1100° C. | 60 seconds | 50 ml/min. |
| incineration | 1100° C. | 1100° C. | 60 seconds | 50 ml/min. |
| atomizing | 2500° C. | 2500° C. | 10 seconds | 30 ml/min. |
| cleaning | 2800° C. | 2800° C. | 4 seconds | 200 ml/min. |

In this example, a predetermined amount (10 μl) of an aqueous solution containing sodium at a predetermined concentration (Na concentration: 10 ppb) was added in a sample of an amount shown in Table 10 below with a micro-syringe so that a sodium-containing resin was prepared, and its sodium concentration was measured. A cuvette used here was a graphite made cuvette. Ar was used as a carrier gas. The results are shown in Table 10 below:

[TABLE 10]

| Sample | Added Na | Detected Na | Recovered Na | Recovery |
|---|---|---|---|---|
| 2.16 mg | — | 5 pg | — | — |
| 2.27 mg | 100 pg | 102 pg | 97 pg | 97% |
| 2.84 mg | 100 pg | 97 pg | 92 pg | 92% |
| 3.47 mg | 100 pg | 100 pg | 95 pg | 95% |

"Added Na" means an amount of Na contained in the added aqueous solution.

"Detected Na" means a detected amount of Na converted from an Na concentration measurement practically obtained by the method according to the present invention.

"Recovered Na" means a difference amount of the Detected Na amount minus an amount of Na of the resin without the addition of Na (namely, the Detected Na amount minus an amount of Na originally contained in the resin).

Recovery=(Recovered Na / Added Na)×100

Example 6

Using the same apparatus as in Example 1, quantitative measurement of trace potassium contained in a fluorine-containing polymer was carried out according to the method of the present invention.

The fluorine-containing polymer used in this example was a PTFE.

Incineration conditions and atomizing conditions of this examples are shown in Table 11 below:

[TABLE 11]

| Treatment Step | Initial Heating Temperature | Final Heating Temperature | Heating Period | Carrier Gas Amount |
|---|---|---|---|---|
| drying | 80° C. | 150° C. | 50 seconds | 200 ml/min. |
| incineration | 800° C. | 1000° C. | 60 seconds | 50 ml/min. |
| incineration | 1000° C. | 1100° C. | 60 seconds | 50 ml/min. |
| incineration | 1100° C. | 1100° C. | 60 seconds | 50 ml/min. |
| incineration | 1100° C. | 1100° C. | 60 seconds | 50 ml/min. |
| atomizing | 2200° C. | 2200° C. | 10 seconds | 30 ml/min. |
| cleaning | 2500° C. | 2500° C. | 4 seconds | 200 ml/min. |

In this example, a predetermined amount (10 µl) of an aqueous solution containing potassium at a predetermined concentration (K concentration: 10 ppb) was added in a sample of an amount shown in Table 12 below with a micro-syringe so that a potassium-containing resin was prepared, and its potassium concentration was measured. A cuvette used here was a graphite made cuvette. Ar was used as a carrier gas. The results are shown in Table 12 below:

[TABLE 12]

| Sample | Added K | Detected K | Recovered K | Recovery |
|---|---|---|---|---|
| 2.44 mg | — | 3 pg | — | — |
| 3.14 mg | 100 pg | 93 pg | 90 pg | 90% |
| 3.08 mg | 100 pg | 88 pg | 85 pg | 85% |
| 2.65 mg | 100 pg | 104 pg | 101 pg | 101% |

"Added K" means an amount of K contained in the added aqueous solution.

"Detected K" means a detected amount of K converted from a K concentration measurement practically obtained by the method according to the present invention.

"Recovered K" means a difference amount of the Detected K amount minus an amount of K of the resin without the addition of K (namely, the Detected K amount minus an amount of K originally contained in the resin).

Recovery=(Recovered K / Added K)×100

Example 7

Using the same apparatus as in Example 1, quantitative measurement of trace magnesium contained in a fluorine-containing polymer was carried out according to the method of the present invention.

The fluorine-containing polymer used in this example was a PTFE (molecular weight: about eight million).

Incineration conditions and atomizing conditions of this examples are shown in Table 13 below:

[TABLE 13]

| Treatment Step | Initial Heating Temperature | Final Heating Temperature | Heating Period | Carrier Gas Amount |
|---|---|---|---|---|
| drying | 50° C. | 100° C. | 60 seconds | 200 ml/min. |
| drying | 100° C. | 130° C. | 60 seconds | 200 ml/min. |
| incineration | 800° C. | 1000° C. | 60 seconds | 50 ml/min. |
| incineration | 1000° C. | 1100° C. | 60 seconds | 50 ml/min. |
| incineration | 1100° C. | 1100° C. | 60 seconds | 50 ml/min. |
| incineration | 1100° C. | 1200° C. | 60 seconds | 50 ml/min. |
| atomizing | 2300° C. | 2300° C. | 10 seconds | 30 ml/min. |
| cleaning | 2600° C. | 2600° C. | 4 seconds | 200 ml/min. |

In this example, a predetermined amount (10 µl) of an aqueous solution containing magnesium at a predetermined concentration (Mg concentration: 10 ppb) was added in a sample of an amount shown in Table 14 below with a micro-syringe so that a magnesium-containing resin was prepared, and its magnesium concentration was measured. A cuvette used here was a graphite made cuvette. Ar was used as a carrier gas. The results are shown in Table 14 below:

[TABLE 14]

| Sample | Added Mg | Detected Mg | Recovered Mg | Recovery |
|---|---|---|---|---|
| 4.05 mg | — | 12 pg | — | — |
| 3.06 mg | 100 pg | 108 pg | 99 pg | 99% |
| 2.30 mg | 100 pg | 109 pg | 102 pg | 102% |
| 2.34 mg | 100 pg | 105 pg | 98 pg | 98% |

"Added Mg" means an amount of Mg contained in the added aqueous solution.

"Detected Mg" means a detected amount of Mg converted from an Mg concentration measurement practically obtained by the method according to the present invention.

"Recovered Mg" means a difference amount of the Detected Mg amount minus an amount of Mg of the resin without the addition of Mg (namely, the Detected Mg amount minus an amount of Mg originally contained in the resin).

Recovery=(Recovered Mg / Added Mg)×100

Example 8

Using the same apparatus as in Example 1, quantitative measurement of trace iron contained in a fluorine-containing polymer was carried out according to the method of the present invention.

The fluorine-containing polymer used in this example was a PTFE (molecular weight: about eight million).

Incineration conditions and atomizing conditions of this examples are shown in Table 15 below:

[TABLE 15]

| Treatment Step | Initial Heating Temperature | Final Heating Temperature | Heating Period | Carrier Gas Amount |
|---|---|---|---|---|
| drying | 80° C. | 130° C. | 60 seconds | 200 ml/min. |
| incineration | 1000° C. | 1100° C. | 60 seconds | 50 ml/min. |
| incineration | 1100° C. | 1100° C. | 60 seconds | 50 ml/min. |
| incineration | 1100° C. | 1100° C. | 60 seconds | 50 ml/min. |
| incineration | 1100° C. | 1100° C. | 60 seconds | 50 ml/min. |
| atomizing | 2700° C. | 2700° C. | 10 seconds | 30 ml/min. |
| cleaning | 2800° C. | 2800° C. | 4 seconds | 200 ml/min. |

In this example, a predetermined amount (5 or 10 μl) of an aqueous solution containing iron at a predetermined concentration (Fe concentration: 1 ppb) was added in a sample of an amount shown in Table 16 below with a micro-syringe so that a potassium-containing resin was prepared, and its magnesium concentration was measured. A cuvette used here was a graphite made tube cuvette which had been subjected to a pyro-treatment. Ar was used as a carrier gas. The results are shown in Table 16 below:

[TABLE 16]

| Sample | Added Fe | Detected Fe | Recovered Fe | Recovery |
|---|---|---|---|---|
| 5.23 mg | — | 11 pg (2.1 ppb) | — | — |
| 4.89 mg | 10 pg (corresponding to 2.0 ppb) | 19 pg (3.9 ppb) | 9 pg (1.8 ppb) | 90% |
| 5.76 mg | 10 pg (corresponding to 1.7 ppb) | 19 pg (3.3 ppb) | 7 pg (1.2 ppb) | 71% |
| 4.77 mg | 5 pg (corresponding to 1.0 ppb) | 14 pg (2.9 ppb) | 4 pg (0.8 ppb) | 80% |
| 4.31 mg | 5 pg (corresponding to 1.2 ppb) | 13 pg (3.0 ppb) | 4 pg (0.9 ppb) | 75% |

"Added Fe" means an amount of Fe contained in the added aqueous solution.

"Detected Fe" means a detected amount of Fe converted from an Fe concentration measurement practically obtained by the method according to the present invention.

"Recovered Fe" means a difference amount of the Detected Fe amount minus an amount of Fe of the resin without the addition of Fe (namely, the Detected Fe amount minus an amount of Fe originally contained in the resin).

Recovery=(Recovered Fe / Added Fe)×100

From the above results, it is seen that even a concentration of about 1 ppb can be quantitatively determined by the method of the present invention.

Comparative Example 1

Quantitative determination for iron of a fluorine-containing polymer was carried out by incinerating the polymer in a platinum made evaporating dish, then dissolving a metal content left therein into $HNO_3$ to obtain a solution, and then measuring an iron concentration of the solution with an atomic absorption spectrophotometry. The fluorine-containing polymer in this Comparative Example was PTFE (molecular weight: about 8 million), An aqueous solution containing iron in a predetermined concentration (Fe concentration: 100 ppb) was mixed with a polymer sample so that the sample contained a predetermined amount of iron. In addition, $Na_2SO_4$ solution of 0.1% by weight was added to the sample so that the sample included 1.5 g of $Na_2SO_4$.

The sample was incinerated under a heating temperature of 600° C. for a heating period of 2 hours. After the incineration, a metal content was dissolved into 1% $HNO_3$ aqueous solution and then the atomic absorption spectrophotometry was carried out. The results are shown in Table 17 below:

[TABLE 17]

| Sample | Added Fe | Detected Fe | Recovery |
|---|---|---|---|
| 0 g | 200 μg | 199 μg | 99% |
| 0 g | 200 μg | 151 μg | 76% |
| 0 g | 250 μg | 200 μg | 80% |
| 1.5 g | 250 μg | 126 μg | 50% |
| 1.5 g | 500 μg | 278 μg | 56% |
| 1.5 g | 500 μg | 259 μg | 52% |

In this Comparative Example, since the amount of Fe is much larger compared with Example 1, the determination with the Fe addition was not carried out.

From the above results, it is clearly seen that the recovery in the quantitative determination of iron contained in the fluorine-containing polymer is much worse compared with the method of the present invention.

Example 9

As in Example 1, quantitative measurement of trace iron contained in a fluorine-containing polymer was carried out according to the method of the present invention.

The fluorine-containing polymer used in this example was an ethylene/tetrafluoroethylene copolymer (ETFE, molecular weight: about 200 thousand).

Incineration conditions and atomizing conditions of this examples are shown in Table 18 below:

[TABLE 18]

| Treatment Step | Initial Heating Temperature | Final Heating Temperature | Heating Period | Carrier Gas Amount |
|---|---|---|---|---|
| drying | 50° C. | 130° C. | 60 seconds | 200 ml/min. |
| incineration | 400° C. | 600° C. | 60 seconds | 50 ml/min. |
| incineration | 600° C. | 650° C. | 60 seconds | 50 ml/min. |
| incineration | 650° C. | 700° C. | 60 seconds | 50 ml/min. |
| incineration | 700° C. | 800° C. | 60 seconds | 50 ml/min. |
| incineration | 800° C. | 1100° C. | 60 seconds | 50 ml/min. |
| incineration | 1100° C. | 1100° C. | 60 seconds | 50 ml/min. |
| atomizing | 2700° C. | 2700° C. | 10 seconds | 30 ml/min. |
| cleaning | 2800° C. | 2800° C. | 4 seconds | 200 ml/min. |

In this example, a predetermined amount (10 μl) of an aqueous solution containing iron at a predetermined concentration (Fe concentration: 20 ppb) was added in a sample of an amount shown in Table 19 below with a micro-syringe so that a potassium-containing resin was prepared, and its magnesium concentration was measured. A cuvette used here was a graphite made tube cuvette which had been subjected to a pyro-treatment. Ar was used as a carrier gas. The results are shown in Table 19 below:

[TABLE 19]

| Sample | Added Fe | Detected Fe | Recovered Fe | Recovery |
|---|---|---|---|---|
| 3.25 mg | — | 61 pg | — | — |
| 2.78 mg | 200 pg | 218 pg | 166 pg | 83% |
| 4.21 mg | 200 pg | 261 pg | 182 pg | 91% |
| 4.05 mg | 200 pg | 246 pg | 170 pg | 85% |

"Added Fe" means an amount of Fe contained in the added aqueous solution.

"Detected Fe" means a detected amount of Fe converted from an Fe concentration measurement practically obtained by the method according to the present invention.

"Recovered Fe" means a difference amount of the Detected Fe amount minus an amount of Fe of the resin without the addition of Fe (namely, the Detected Fe amount minus an amount of Fe originally contained in the resin).

Recovery=(Recovered Fe / Added Fe)×100

From the above results, it is seen that there occurs no adverse effect on the recovery even when the incineration period is set longer.

Comparative Example 2

Quantitative determination of iron contained in a fluorine-containing polymer was carried out as in Example 1 except that no iron was added and that the incineration conditions were as shown in Table 20 below:

[TABLE 20]

| Treatment Step | Initial Heating Temperature | Final Heating Temperature | Heating Period | Carrier Gas Amount |
|---|---|---|---|---|
| drying | 80° C. | 120° C. | 30 seconds | 200 ml/min. |
| incineration | 1100° C. | 1100° C. | 60 seconds | 50 ml/min. |
| atomizing | 2700° C. | 2700° C. | 10 seconds | 30 ml/min. |
| cleaning | 2800° C. | 2800° C. | 4 seconds | 200 ml/min. |

As shown in Table 21 below, no iron was detected in this Example.

[TABLE 21]

| Sample | Detected Fe | Recovered Fe | Recovery |
|---|---|---|---|
| 2.39 mg | not detected | — | — |
| 2.78 mg | not detected | — | — |

"Not detected" means that the spectrophotometer indicated a clearly strange measurement.

The reason why no iron was detected is that the polymer remained due to the shorter incineration period which leads to the insufficient incineration and such a polymer was decomposed and volatilized at once during the atomizing step which resulted in fuming and irregular reflection of light, so that the spectrophotometer indicated the measurement as if there occurred absorption.

Example 10

Quantitative determination of iron contained in a fluorine-containing polymer was carried out as in Example 1 except that the polymer was replaced with a tetrafluoroethylene/perfluoro(propyl vinyl ether) copolymer (PFA, molecular weight: about 300 thousand).

The results are shown in Table 22 below:

[TABLE 22]

| Sample | Added Fe | Detected Fe | Recovered Fe | Recovery |
|---|---|---|---|---|
| 2.98 mg | — | 65 pg | — | — |
| 2.53 mg | 200 pg | 230 pg | 174 pg | 87% |
| 4.88 mg | 200 pg | 269 pg | 162 pg | 81% |
| 3.21 mg | 200 pg | 241 pg | 170 pg | 85% |

"Added Fe" means an amount of Fe contained in the added aqueous solution.

"Detected Fe" means a detected amount of Fe convened from an Fe concentration measurement practically obtained by the method according to the present invention.

"Recovered Fe" means a difference amount of the Detected Fe amount minus an amount of Fe of the resin without the addition of Fe (namely, the Detected Fe amount minus an amount of Fe originally contained in the resin).

Recovery=(Recovered Fe / Added Fe)×100

Example 11

Quantitative determination of iron contained in a fluorine-containing polymer was carried out as in Example 1. In this example, after the incineration period of Example 1 (totally 240 seconds), the temperature was kept at that incineration temperature (1100° C.) for further 960 seconds (thus a total incineration period was 1200 seconds), and then atomizing was carried out followed by the iron concentration measurement. The iron recovery was 90 %. This proves that there is no adverse effect on the recovery even though the incineration period is extended.

Example 12

Using the same apparatus as in Example 1, quantitative determination of iron contained in a fluorine-containing polymer (PTFE, molecular weight: about eight million) was carried out eight times according to the method of the present invention without the addition of iron. The results are shown in Table 23 below. The incineration conditions and the atomizing conditions were the same as those in Example 8.

[TABLE 23]

| Sample Amount | Detected Fe Amount | Fe concentration |
|---|---|---|
| 5.3 mg | 11.1 pg | 2.1 ppb |
| 6.0 mg | 13.8 pg | 2.3 ppb |
| 3.9 mg | 7.4 pg | 1.9 ppb |
| 4.4 mg | 7.9 pg | 1.8 ppb |
| 5.1 mg | 12.2 pg | 2.4 ppb |
| 5.1 mg | 10.2 pg | 2.0 ppb |
| 5.4 mg | 11.3 pg | 2.1 ppb |
| 6.5 mg | 14.3 pg | 2.2 ppb |

From Table 23, an average Fe concentration and a standard deviation was calculated:

| Average Fe concentration | 2.1 ppb |
|---|---|
| Standard deviation | 0.2 |

Then, a detection limit (=3σ (standard deviation)) of the present method was estimated to be 0.6 ppb (3×0.2) with reference to L. H. Keith, Analytical Chemistry (Anal. Chem.), 55, 2210 (1983).

I claim:

1. A method for the quantitative determination of a trace amount of a metal impurity contained in a fluorine-containing polymer using a flameless atomic absorption spectrophotometer wherein, depending on a kind of a metal to be quantitatively determined, a predetermined amount of a sample of the polymer is incinerated under incineration conditions including an incineration temperature in the range of about 400° to 1200° C. and an incineration period of at least about 100 seconds, and then an absorbance of the incinerated sample is measured using the flameless atomic absorption spectrophotometer.

2. The method according to claim 1 wherein the fluorine-containing polymer is a polytetrafluoroethylene, a tetrafluoroethylene/perfluoro(propyl vinyl ether) copolymer, a tetrafluoroethylene/hexafluoropropylene copolymer, a tetrafluoroethylene/ethylene copolymer, a polyvinylidene fluoride, a polyvinyl fluoride, a vinylidene fluoride/tetrafluoroethylene/hexafluoropropylene copolymer, a vinylidene fluoride/hexafluoropropylene copolymer, a tetrafluoroethylene/perfluoro(methyl vinyl ether) copolymer, a tetrafluoroethylene/perfluoro(propoxyl vinyl ether) copolymer or a perfluoropolyether.

3. The method according to claim 1 wherein the metal to be quantitatively determined is Fe, Cr, Ni, Cu, Na, K, Mg, Ca, Co, Zn, Mn or Al.

4. A process for the production of a fluorine-containing polymer characterized in that a trace amount of a metal impurity contained in the fluorine-containing polymer is quantitatively monitored by means of the method according to claim 1.

5. A process for the production of a fluorine-containing polymer characterized in that a trace amount of a metal impurity contained in the fluorine-containing polymer is quantitatively determined by means of the method according to claim 1.

* * * * *